United States Patent [19]

Heinz et al.

[11] Patent Number: 4,979,507
[45] Date of Patent: Dec. 25, 1990

[54] ENERGY SAVING CARDIAC PACEMAKER

[75] Inventors: Michael E. Heinz; Heinz P. Theres, both of Munich, Fed. Rep. of Germany

[73] Assignee: Eckhard Alt, Ottobrunn, Fed. Rep. of Germany

[21] Appl. No.: 347,435

[22] Filed: May 3, 1989

[30] Foreign Application Priority Data

May 10, 1988 [DE] Fed. Rep. of Germany ....... 3816042

[51] Int. Cl.$^5$ ............................................. A61N 1/362
[52] U.S. Cl. .......................................... 128/419.0 PG
[58] Field of Search .............. 128/419 PG, 419 P, 697

[56] References Cited

U.S. PATENT DOCUMENTS

| | | | |
|---|---|---|---|
| 3,517,663 | 6/1970 | Bowers et al. | 128/419 PG |
| 3,669,120 | 6/1972 | Nielsen | 128/419 PG |
| 3,713,449 | 1/1973 | Mulier | 128/419 PG |
| 3,717,152 | 2/1973 | Van Den Berg | 128/419 PG |
| 3,757,792 | 9/1973 | Mulier et al. | 128/419 PG |
| 3,777,762 | 12/1973 | Nielsen | 128/422 |
| 3,949,758 | 4/1976 | Jirak | 128/419 PG |
| 4,340,063 | 7/1982 | Maurer | 128/421 |
| 4,571,589 | 2/1986 | Slocum et al. | 128/419 PG |

*Primary Examiner*—William E. Kamm
*Assistant Examiner*—Kennedy J. Schaetzle
*Attorney, Agent, or Firm*—Laurence R. Brown

[57] ABSTRACT

This invention has as an objective the universal matching of individual patient-pacemaker-implant electrode interface conditions to follow dynamic changes occurring in use, from pacemaker to pacemaker and from patient to patient to control the pacing pulse energy in operation most efficiently to prolong battery life. Information from the implanted stimulation electrode is analyzed to discriminate the energy level of pulses effective and ineffective to stimulate a heartbeat for at least two different stimulation pulse characteristics. This analyzed information is automatically processed in logic circuits to conform with the requirements of particular pacemaker adjustments to develop an optimized energy pacing pulse with adequate safety margin. Programming and logic equipment can be in the pacemaker, but additional energy saving with those calculations takes place when it is external to the pacemaker and bidirectional communication of information takes place with the pacemaker. Periodic automatic programming can take place in implanted pacemaker installations for continuous long term monitoring and control to obtain the optimum battery life and adequate safety standards.

18 Claims, 5 Drawing Sheets

ENERGY SAVING CARDIAC PACEMAKER

TECHNICAL FIELD

The present invention relates to implanted battery operated cardiac pacemakers employing battery energy saving features, and more particularly it relates to means and methods for monitoring an implanted pacemaker to determine a minimum energy threshold stimulus pulse characteristic and for controlling the stimulus pulse characteristics accordingly to reduce battery consumption.

BACKGROUND ART

Great technical improvements have been achieved in the almost thirty years of cardiac pacemaker therapy. Not only has the longevity of pacemaker aggregates increased from a few months to several years, at the same time there has been a significant reduction in size. Multiprogrammable pacemakers have been made possible by modern microelectronics.

U.S. Pat. No. 4,485,818 describes a multiprogrammable pacemaker on the basis of a microprocessor. The use of lithium batteries, that are more favorable in terms of energy and have replaced the formerly customary zinc-mercury batteries with high self-discharge, has contributed to a further reduction in pacemaker size and longer longevity. Energy saving circuitry measures have reduced the pacemaker's current consumption. The development of modern electrodes that build up very small polarization voltages has also contributed to reducing the energy required for pacing.

The pacing and excitation of the cardiac muscle is subject to the laws of electrophysiology, according to which a relation is known between pulse width, which is necessary for exciting the heart and pulse amplitude. The stimulus threshold curve is an individual parameter, which results from the interference of the particular pacemaker patient's heart and the electrode. The stimulus threshold curve is not a fixed parameter, but is influenced by many different factors. These include the size, surface and nature of the electrode. The nature of the heart also plays a crucial part. In addition to these predetermined influencing factors, there are a large number of continuously changing influencing factors such as drug effects, the perfusion conditions in the heart under various working conditions, epinephrine levels in the body, diurnal variations and the type of pacing (uni- or bipolar) as well as the length of time an electrode has been implanted. These parameters have an essential influence on the individual stimulus threshold curve. Further information can be found e.g. in Alt "Schrittmachertherapie des Herzens", perimed Verlag, Erlangen, 1985, pp. 33–39 and in Ripart and Muciga "Electrode Heart Interface: Definition of the Ideal Electrode", Pace, Vol. 6, March 1983 pages 410 to 421.

Since numerous factors have a continuously changing influence on the stimulus threshold curve, the energy delivery of a pacemaker system must do justice to these fluctuations. A so-called 100% safety margin is generally set, which means that the energy delivered for pacing should be 100% higher than the minimum amount of energy necessary for exciting the heart at the time of control. The energy consumption per pacing pulse is a function of the voltage, the current and the duration of the stimulus. Assuming constant resistance, the energy consumption can also be stated as:

$$W = U^2 \times t/R \quad (1)$$

In accordance with the stimulus threshold curve, a certain minimum product of voltage or current and duration of effect (pulse width) is always necessary, which is described by the familiar equation of the stimulus threshold curve:

$$U = U_0(1 + t_c/t) \quad (2)$$

$U_o$ is the voltage rheobase, the time of chronaxie $t_c$ corresponds to the pulse width at twice the rheobase voltage. Assuming a constant resistance R and combining Equations 1 and 2, one sees that the energy is lowest at the time of chronaxie $t_c$, being $$W(t_c) = 4U_o^2 t_c/R \quad (3)$$

On the other hand, a reduction of the pulse width oppositely has higher energy consumption due to a compensatory necessary increase in voltage. For example, a reduction of the pulse width to one tenth of the chronaxie requires a compensatory increase in voltage U. From Equation 2 above, the voltage U necessary in this type of pacing is eleven times $U_o$.

This results in a total energy of $$W = 12.1 U_o^2 t_c/R.$$

Compared to the energy $W(t_c)$ at the optimal time $t_c$ (see Equation 3), the required amount of energy in the stated case is more than 300% the energy for pacing at the time of chronaxie. It is obvious that this energy consumption has considerable influence on the longevity of the pacemaker.

In order to obtain sufficient reliability despite the varying stimulus threshold, measures have been developed in the past for determining the stimulus threshold even after implantation.

U.S. Pat. No. 3,777,762 describes a method for non-invasive monitoring of the stimulus threshold by continuously reducing the pulse amplitude.

U.S. Pat. No. 4,305,396 describes a pacemaker which is able to distinguish between effective and ineffective pacing pulses on the basis of the after-potential variations.

The article "The Autodiagnostic Pacemaker" by A. Auerbach in PACE, Vol. 2, pp. 58 to 68, 1979, describes an autodiagnostic pacemaker which is also able to distinguish between effective and ineffective pacing pulses. A similar method is described by H. J. Thalen in the article "Evoked Response Sensing as Automatic Control of the Pacemaker Output" in G. A. Feruglio: Cardiac Pacing, Piccin Medical Books, Padua 1982, pp. 1229 to 1234.

The idea of automatically detecting the stimulus threshold does justice to the idea of safety, to prevent the pacemaker pulses from being rendered ineffective by an incorrectly low adjustment of the delivered energy and the patient from therefore undergoing asystole possibly being life threatening.

However, none of these papers indicates at what time, i.e. at which pulse width and at which pulse amplitude, a given patient is best treated with regard to energy saving operation as well as maximum safety.

The present invention is based on the problem of providing means for a cardiac pacemaker which adapts the individual energy demand necessary for safe and effective pacing to the particular possible minimum, and thus optimally utilizes the available electrical energy, thereby allowing for an even smaller pacemaker that imposes even less of a strain on the patient.

This problem is solved according to the invention in accordance with the embodiments set forth in the following specification, claims and the accompanying drawing.

The invention is thus based on the finding that if the pacemaker, or the controlling external programming system, independently measures the stimulus threshold and measurements are taken at different pulse widths and pulse amplitudes, one can determine the rheobase, which can be described as a current rheobase or as a voltage rheobase ($I_o$ or $U_o$). As a further means to calculate the minimum energy needed for effective pacing, the internal current consumption at the pacemaker's battery can be considered as well. In conjunction with low polarizing electrodes, one can likewise determine the chronaxie with sufficient confidence by at least two measurements with different pulse widths or pulse amplitudes. Pacing with a pulse width corresponding to the chronaxie constitutes the optimal energy consumption. The repeated detection of stimulus threshold values and the chronaxie contributes to adapting the pulse delivery and thus the energy delivery to the changing needs of the patient. It makes no difference for the individual pacemaker what electrode is used to pace the heart, which means, for example, that older electrodes with poorer energy consumption are checked for optimal pacing properties just as more favorable modern electrodes are. The repeated determination of the corresponding parameters also allows for adaptation to the different fluctuations over time in the stimulus threshold curve within the individual patient. One is aware, for example, of diurnal variations of the stimulus threshold curve, drug effects, changes in the electrolyte metabolism and changes in the stimulus threshold due to intermittent cardiac ischemia. Since more than half of all pacemaker patients suffer from perfusion insufficiency in the cardiac muscle, this aspect is of major importance.

The invention can also be used in connection with an external programming device. The stimulus threshold of the particular pacemaker patient is determined by common programming and telemetry methods. A special logic in the external programming device performs measurements according to the invention and determines the most energy efficient pulse duration and pulse amplitude within an individual patient by performing automatically several, at least two, measurements of the threshold value at varying pulse widths and amplitudes. By means of constant bidirectional telemetry and transmission of the intracardiac signal from the pacemaker to the external programming unit the program unit is capable to the intracardiac signal with respect to effective and ineffective pacing impulses delivered to the heart from the implanted pacemaker, but under control of the external programming unit. In case of the first evidence of a pacing impulse to be ineffective, the energy delivered to the heart is instantaneously increased again in order to prevent the pacemaker bearer from prolonged asystolic episodes. The data is fit into the formula for the calculation of the most energy effective individual setting, above noted, with appropriate safety margin. After the external programming unit has performed this determination of the optimal energy setting for an individual heart-electrode configuration, it also takes into consideration the internal technical situation within a given pacemaker model as far as the practical technical possibilities are concerned to select a theoretically optimal energy effective setting, since those data of different models of manufacture are stored within the logic of an external programming unit. A comparison is then made of the best theoretical value with the best practical realizable value for the equipment and accordingly a pulse width and amplitude setting is selected that is practically the best as far as energy efficiency is concerned, even though this might differ slightly from the theoretically best setting. A calculation of a safety margin is also performed. This practically best setting for values of pulse width and amplitude including a safety margin is shown on a display in the programming unit. After confirmation by the supervising physician or pacemaker clinitian (nurse, or technician) this setting is transmitted to the implanted pacemaker and the pacemaker is programmed accordingly.

This way of putting the logic circuits required by this invention into an external programming unit, with telemetry communication with the pacemaker, takes into consideration the momentary situation of limited logic available within the pacemaker at present, and the energy drain on the battery in the pacemaker that would be taken if the pacemaker determines the optimal energy by itself.

Further embodiments, features and advantages of the invention may be found throughout the following description.

BRIEF DESCRIPTION OF THE DRAWINGS

The invention is explained in more detail in exemplary embodiments with reference to the drawing, in which.

THE PREFERRED EMBODIMENTS

Figure 1:
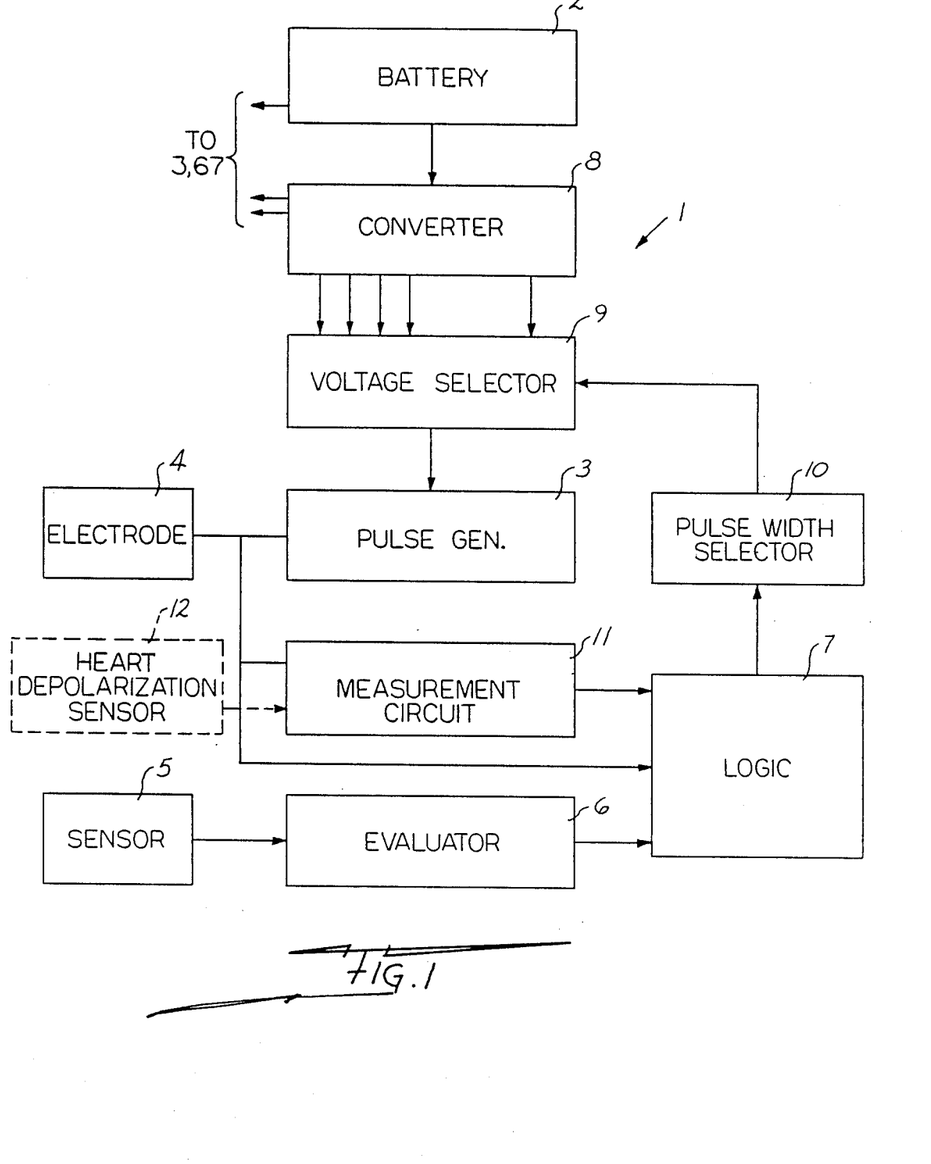
FIG. 1 shows a schematic block diagram of a pacemaker embodiment provided in accordance with this invention.

The essential parts of the cardiac pacemaker 1 are a battery 2, a pulse generator 3, a pacing electrode 4, a sensor 5, an evaluation circuit 6 and a logic circuit 7. Sensor 5 is used to detect one or more physiologic parameters of a pacemaker patient. This sensor may be e.g. a temperature sensor, an activity sensor or a combination of several sensors. The signals of this sensor are evaluated in evaluation circuit 6 and are processed in the logic 7 according to given criteria. The logic then calculates the necessary pacing rate which is adequate to the current work load of the pacemaker patient. The logic then drives pulse generator 3 which accordingly delivers pacing pulses to electrode 4. Battery 2 supplies the various circuit components of the pacemaker with energy. An additional circuit 8 is provided e.g. in the form of voltage divider, which divides the battery voltage into several voltages which can then be used for supplying the individual components of the pacemaker. The converter outputs, which thus carry several voltages, are connected to a selection circuit 9, which can be driven by logic 7. The selection circuit then acts on pulse generator 3. Logic 7 thus determines via selection circuit 9 the voltage amplitude of the pacing pulses for electrode 4. Logic 7 also determines the pulse width of the pacing pulses. On the basis of this calculation, which will be explained below, the logic drives a selection circuit, e.g. in the form of a timer 10, that acts on the pulse generator.

The described pacemaker additionally determines the effectiveness of a given energy applied via an electrode into the heart as far as a depolarization of the heart muscle is concerned by analyzing the de- and re-polarization of the electro-physiologic cardiac events in order to determine the stimulus threshold characteristic of the rheobase and strength-duration characteristics. This can be done, for example, as follows. Logic 7, in response to a program contained therein selected in a threshold determination mode, continuously lowers the pulse width of the pacing pulses by driving pulse generator 3 via selection circuit 10 at a first constant voltage $U_1$ of the pacing pulses, until no further cardiac activity in response to a first series of pacing pulses is registered. This process is repeated at a second voltage $U_2$, or several different voltages. The cardiac activity test is performed with the aid of the implanted pacing stimulus electrode 4, which in this case serves simultaneously as a measuring electrode. The signals (intracardiac ECG, etc.) are fed to a heart depolarization sensor 12 for detecting the effective and ineffective pulses, which delivers corresponding signals to logic 7, which then determines the strength-duration threshold characteristic.

Figure 2:
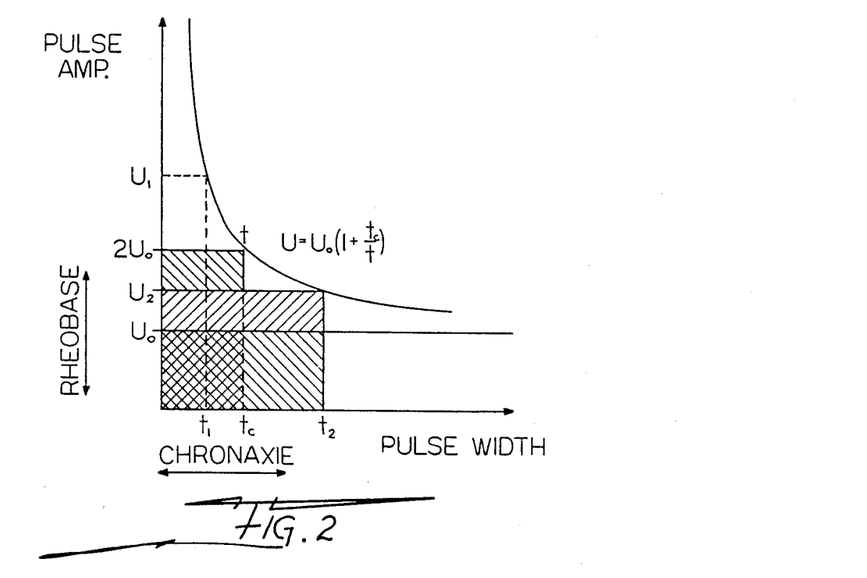
FIG. 2 shows a diagram of the strength-duration characteristic featuring rheobase ($U_o$) and chronaxie ($t_c$)

The determination of the stimulus threshold curve is explained in more detail with reference to FIG. 2. Therein, the pulse amplitude is shown as voltage U versus pulse width t of the pacing pulses. This stimulus threshold curve can be plotted either as a voltage characteristic or as a current characteristic. The formula for the stimulus threshold curve corresponds to Equation 2 above. The corresponding current characteristic is of the same shape, with the voltage values being replaced by current values. The stimulus threshold curve has the form of a hyperbole shifted in the positive direction in the quadrant about the value $U_o$. In order to determine the pulse width and pulse amplitude for the pacing pulses at minimal energy, one determines the stimulus threshold e.g. at two fixed voltages $U_1$ and $U_2$ by varying the pulse width with the aid of logic 7 via selection circuit 10 until cardiac activity in response to pacing is just barely present. From this the associated pulse widths $t_1$ and $t_2$ then are known. Pulse width $t_2$ is a multiple of pulse width $t_1$. On the basis of Equation 2 above, the following formulae result for the two known voltages $U_1$ and $U_2$:

$$U_1 = U_o(1 + t_c/t_1) \text{ and } U_2 = (U_o(1 + t_c/kt_1)) \quad (4)$$

Reformulation of these equations results in the values of $U_o$:

$$U_o = (kU_2 - U_1)/(k - 1) \quad (5)$$

and this value of the chronaxie:

$$t_c = (U_1 - U_o)t_1/U_o \quad (6)$$

Figure 3:
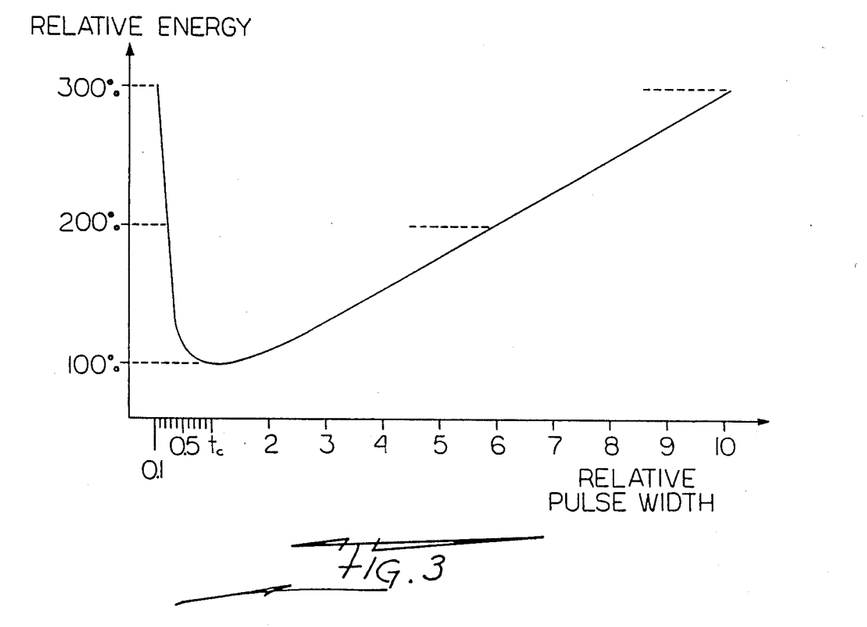
FIG. 3 shows a diagram of the relative energy consumption of a pacemaker for pacing a heart at different relative pulse widths presented as multiple times of chronaxie $t_c$.

With modern low polarizing electrodes, it is thus only necessary to measure two points on the stimulus threshold curve to determine the chronaxie and the corresponding pacing voltage $2U_o$ with adequate accuracy. Pacing of the heart with pulses of these values would be just sufficient and show the lowest energy consumption. This can be also seen by FIG. 3 which shows the energy consumption for the stimulus threshold curve in FIG. 2. It can be seen that the energy consumption is lowest with pulses whose width corresponds to chronaxie, increasing very rapidly with pulses of shorter width and increasing gradually with pulses of greater width than $t_c$. A reduction of pulse widths to values below $t_c$ requires a compensatory increase in voltage resulting in a steep increase of the relative energy needed for effective depolarization from the pacing pulses.

It is of course unsuitable to perform pacing with these minimum and just barely effective values since they are situated directly on the stimulus threshold curve. For these reasons one adds a safety margin in order to achieve reliable pacing of the heart in any case. This can be done by elevating either the voltage amplitude or the pulse width. Due to the determination of the stimulus threshold curve according to the invention and the chronaxie, this safety margin need not exceed 5 to 30% if the threshold is continuously checked by a heart depolarization sensor. The pulse width is preferably elevated accordingly, since the energy required for pacing increases relatively slowly in this range. Such an adjustment aimed at safety with the aid of the pulse width is also much easier to do than to change the voltage level, since the timing circuit and pulse width selector can be easily designed with various graduations to deliver a greater plurality of pulse widths than available from a voltage converter.

Although the design of the circuit for the pacemaker has been described as consisting of discrete elements above, it is of course conceivable for these elements to be functions of a processor, i.e. of the logic in this case.

The described measurements for determining the rheobase-chronaxie and therefrom the optimal pacing in terms of pulse width and pulse amplitude are performed periodically at intervals which are determined by the logic itself. The logic is programmed in such a way that these measurements are performed after implantation of a pacemaker relatively frequently, e.g. every hour or every half a day. This makes it possible to consider changes of the rheobase e.g. due to diurnal variations and especially after implantation of the pacemaker. After a certain time the rheobase stabilizes and the changes in the rheobase are determined essentially by diurnal variations. Once this stabilized phase is reached, the measurements can be performed at larger intervals, which is also controlled by logic 7.

Figure 4:
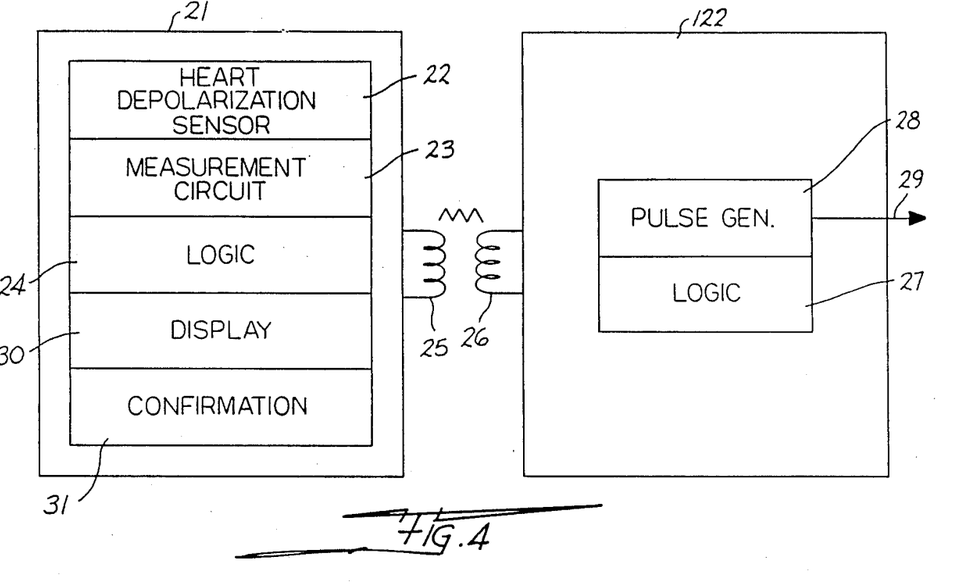
FIG. 4 shows a schematic view of an embodiment with an external programming device and a telemetrically programmable pacemaker.

FIG. 4 shows an external programming device 21 for a pacemaker. The external programming device is used to determine the stimulus threshold and strength-duration characteristics of a pacemaker patient by analyzing the digitized intracardiac ECG signal, delivered via electrode 4 to the pacemaker and transmitted from the pacemaker via telemetry means 26 to the telemetry equipment on the programmer's side 25 to be analyzed in heart depolarization sensor 22. The necessary measurement circuit 23 and a logic 24 are indicated within programming device 21. From the measured values for the stimulus threshold, the optimal pulse width and pulse amplitude for the pacing pulses of the pacemaker are determined within logic 24 as described above, including a certain safety margin. The external programming device also includes telemetry means, transmitter 25 and receiver, for transmitting the calculated data to implanted pacemaker 122. Pacemaker 122 has telemetry means 26 for receiving and transmitting coded data information connected to logic 27. Logic 27 then controls a pulse generator 28 connected to a pacing electrode 29 in this suggested embodiment. The other parts of the pacemaker, such as sensors for physiologic parameters and the associated evaluation circuits, have been omitted in this example, in view of the state of the art hereinbefore set forth showing that the implementation of such embodiments is within the ordinary skill of those in this art. The pulse width and pulse amplitude values of the pacing pulses are calculated in external programming device 21. Since the external programming device is aware of the type and model of the pacemaker, it is communicating with those individual data of the specific pacemaker characteristics activated from logic 24, where data is programmed and stored for the individual internal technical energy characteristics for a range of given models. Since each pacemaker type has its own current consumption in the non-pacing mode, variability of pulse width and pulse amplitude, this also has to be considered when calculating an optimal pacing energy in practice. Those practically most efficient energy values can differ from the theoretically calculated values determined only on an electro physiologic basis without considering the practical in-pacemaker programmability situation and energy efficiency. The theoretically optimum value is compared with the best practically achievable optimal energy value and the corresponding pulse width and pulse amplitude is then displayed in a display 30. These values are checked and, if necessary, changed by an attending physician. To transmit these values to pacemaker 122, there is a control button 31 for activating transmission by the telemetry system. Telemetrically programmable cardiac pacemakers are known as such, so that it is unnecessary to deal with them in any detail here.

Figure 5:
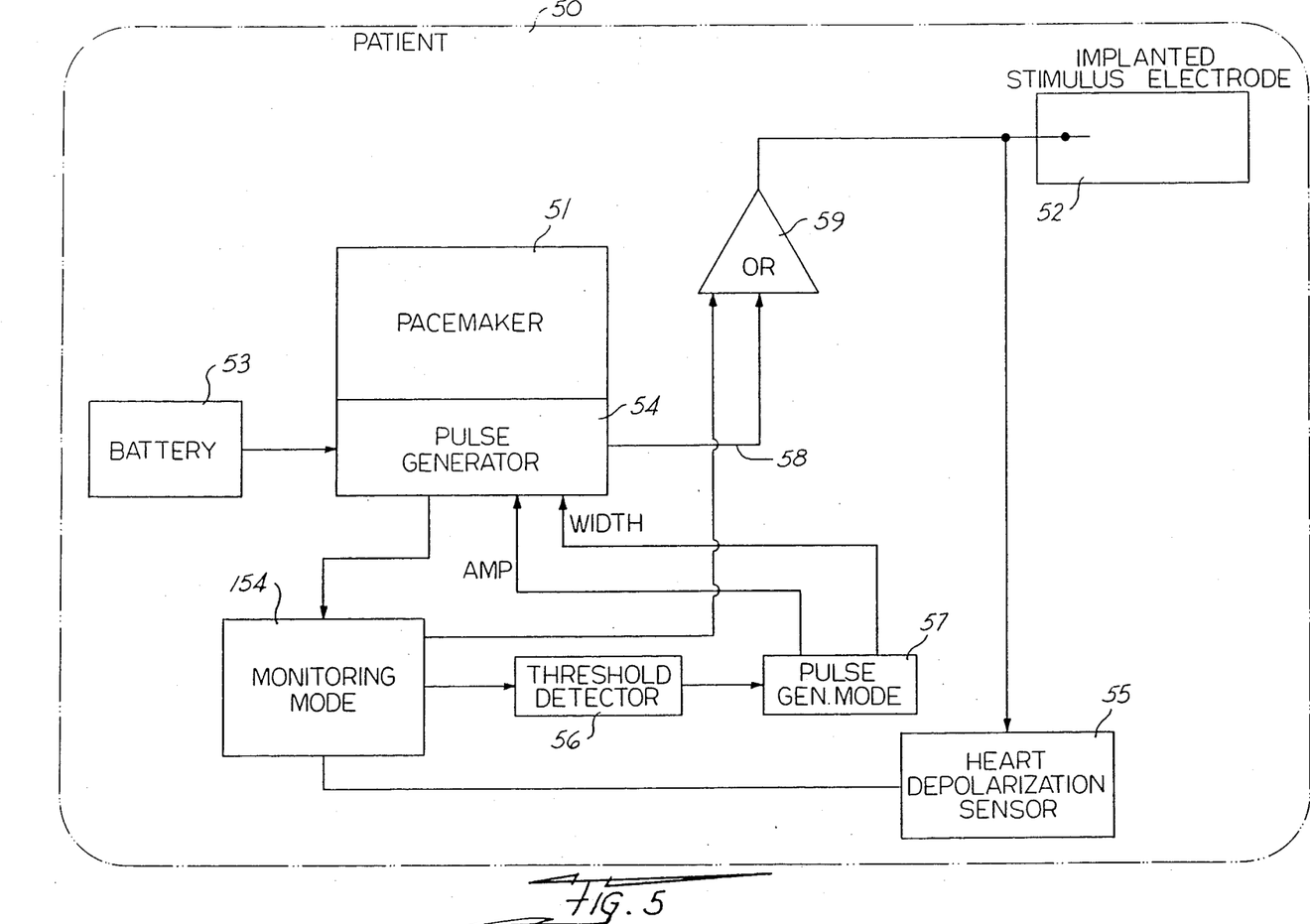
FIG. 5 is a block system diagram of a pacemaker system afforded by this invention.

Now with reference to the general system mode of operation reference is made to the block diagram of FIG. 5. A patient 50 has implanted the pacemaker 51 and the stimulus electrode 52. Critical to this pacemaker is the life of implanted battery 53, which supplies primarily energy for the pulse generator 54 for producing the stimulus pulses transmitted to the pacing electrode 52, but also the other power consuming parts of the pacemaker.

In order to reduce the stimulus pulse energy and thus significantly increase the life of the battery 53 in the manner aforesaid, the heart depolarization effectiveness using at least two different voltages and pulse width settings is sensed from a program supplied in the monitoring mode circuitry 154 by means of a sensor 55, in order to determine periodically the minimum threshold pulse energy determined at detector 56 necessary for inducing a heartbeat. This monitoring circuit program provides a reduction of pulse energy from pulse generator 54 until the heartbeat becomes marginal to signify the energy threshold. The threshold detector according to the above mentioned formulae calculates the threshold at different voltages ($U_1$ and $U_2$) with the corresponding pulse widths ($t_1$ and $t_2$), the optimal energy efficiency setting of the two particular voltages and corresponding pulse widths. That optimal energy setting is stored in the pulse generating mode block 57 for directing the pulse generator 54 to supply pulses of appropriate amplitude and width for conserving battery drain (with the safety factor added) until a further monitor cycle overrules the stored values. Thus while the monitor cycle is in effect the usual pacing pulses from lead 58 are blocked and only the monitoring pulses are used as a function of the OR circuit 59. As aforesaid, it is optional whether the monitoring by means of 54, 55 and 56 is achieved externally with telecommunicating means or internally in the implanted pacemaker. Reduced power drain upon the pacemaker is a significant advantage of the external monitoring unit. In self contained pacemakers the control logic for the monitoring cycles may be simplified and customized for better control of pacemaker optimum energy, and may have periodic reevaluation cycles built in to take into account possible changing conditions without return to a monitoring station. As far the monitoring cycles for optional setting for energy efficiency is concerned it should be clearly understood that a heart depolarization sensor, if incorporated into the pacemaker, is constantly running in order to allow a minimal low energy setting close to the strength-duration curve without a major safety margin, thereto to save additional battery energy.

Figure 6:
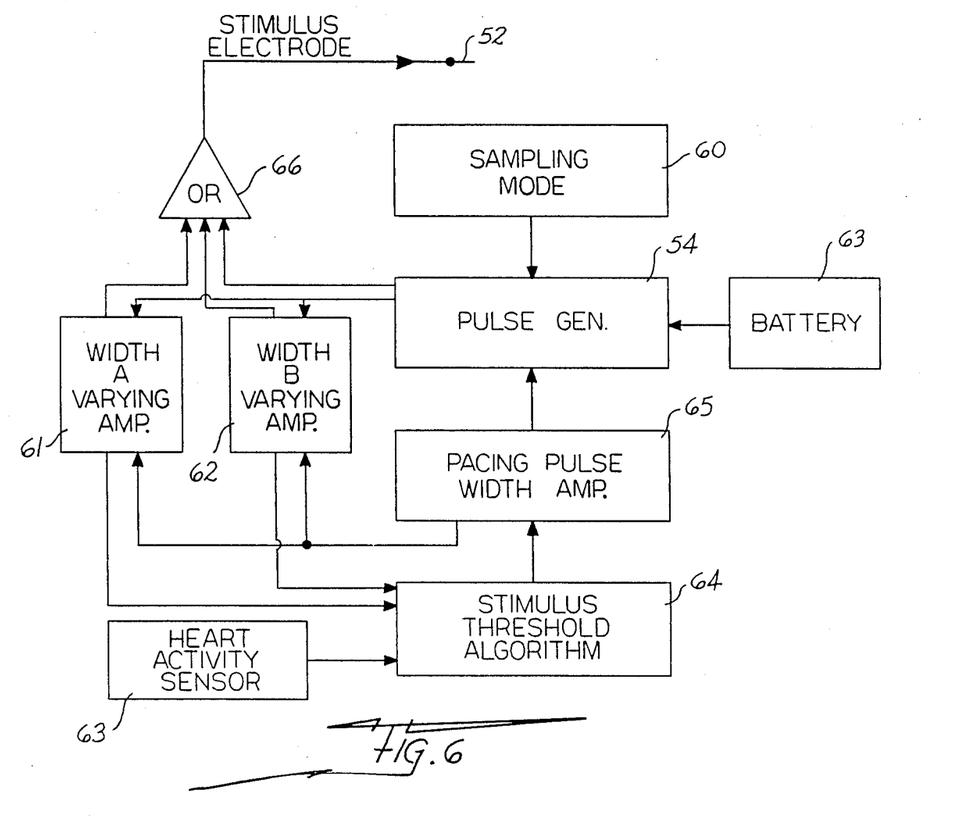
FIG. 6 is a block diagram of a pulse monitoring and control embodiment of the invention.

The block diagram embodiment of FIG. 6 provides an operational flow sequence for the threshold detection and pulse control features of this invention. This circuit accordingly at 61, 62 provides two pulses A and B of different known energy levels from pulse generator 54 when the sampling mode 60 is in effect. As before explained in connection with FIGS. 2 and 3, these two pulses with the help of the heart activity sensor 63 will determine the minimum energy characteristic and result in the derivation of an algorithm 64 for a particular patient and pacemaker system. The derived algorithm therefore establishes an operating pulse energy level, as before stated, preferably a variation of pulse width in circuit 65 for control of the pacing pulses formed in generator 54 as transmitted to the stimulus electrode 52 by way of OR circuit 66 which also transmits the pulses A and B alternatively to the stimulus electrode during the sampling period.

Figure 7:
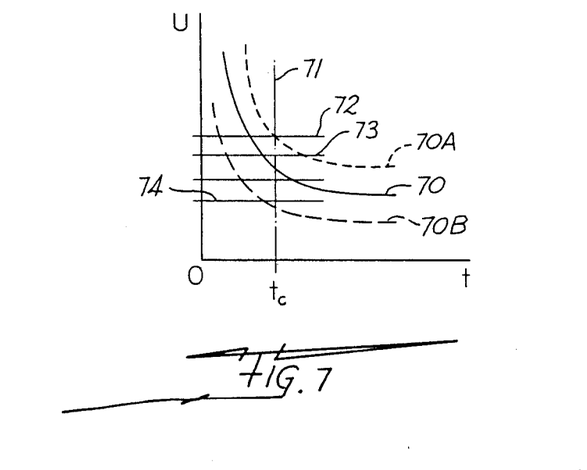
FIG. 7 is a graph similar to FIG. 2 showing the relationship of different individual pacemaker systems that might be encountered.

In FIG. 7, the variations between different implanted electrode are shown by the curves 70A, 70 and 70B related to the time of chronaxie $t_c$. Thus the various voltage operation levels U for the respective pacemaker systems are indicated at 72, 73 and 74 for example.

Figure 8:
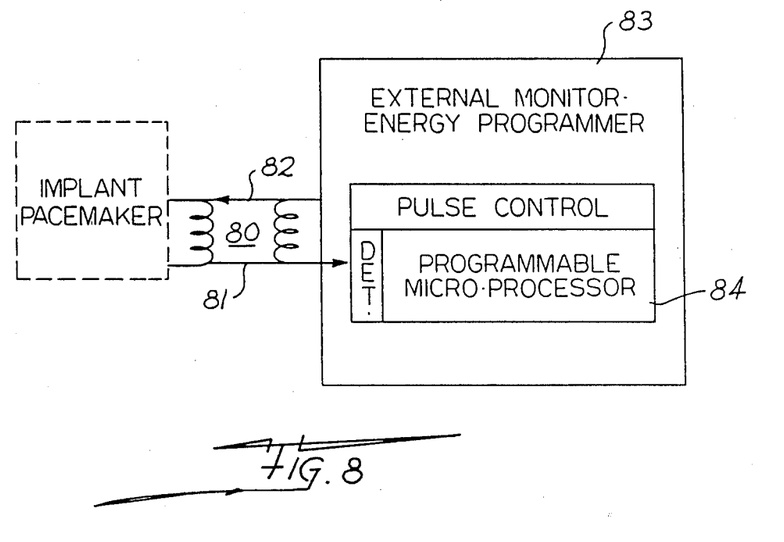
FIG. 8 is a simplified block diagram of a computer controlled energy saving system of this invention using an external monitor programmer under the control of a computer program.

FIG. 8 identifies the hereinbefore described system with an external monitor-programmer 83 operating over a communication link 80 to send information 82 to the implant pacemaker and receive it 81 from the pacemaker. In accordance with the state of the art a microprocessor 84 in the programmer unit may be programmed for the proper control logic and may contain in its memory the stored data relating to the technical characteristics of a range of pacemaker models.

Having therefore improved the state of the art by this invention, those novel features believed descriptive of the spirit and nature of the invention are set forth with particularity in the following claims.

We claim:

1. The method of controlling a battery operated cardiac pacemaker implant to produce low energy pacing stimulus pulses at an implanted heart stimulus electrode to conserve battery power, comprising in combination the steps of:

performing threshold measurements at at least two different stimulus pulse energy levels at the implanted electrode of a particular patient and organizing said stimulus pulses into effective and ineffective energy levels for producing heartbeats, determining from the threshold measurements an individual energy threshold characteristic for the particular pacemaker system and patient under test by calculating from said different energy level measurements a substantially most energy efficient stimulus pulse in the implanted pacemaker effective to stimulate the heart, adjusting the energy efficient stimulus pulse to the technical capability of the particular pacemaker for operating that pacemaker with a modified optimum energy stimulus pulse exceeding the minimum energy threshold by a predetermined safety margin, and producing in the pacemaker said modified stimulus pulse, thereby operating the pacemaker at reduced battery energy drain.

2. The method defined in claim 1 further comprising, periodically monitoring said threshold characteristic in a patient and dynamically producing said modified pacing pulses to follow changes in the monitored threshold characteristic.

3. The method of controlling a battery operated cardiac pacemaker implant to produce low energy pacing stimulus pulses at an implanted heart stimulus electrode to conserve battery power, comprising in combination the steps of:

performing threshold measurements at at least two different stimulus pulse energy levels at the implanted electrode of a particular patient and organizing said stimulus pulses into effective and ineffective energy levels for producing heartbeats, determining from the threshold measurements an individual energy threshold characteristic for the particular pacemaker system and patient under test by calculating from said different energy level measurements a substantially most energy efficient stimulus pulse in the implanted pacemaker effective to stimulate the heart, adjusting the energy efficient stimulus pulse to the technical capability of the particular pacemaker for operating that pacemaker with a modified optimum energy stimulus pulse exceeding the minimum energy threshold by a predetermined safety margin, producing in the pacemaker said modified stimulus pulse, thereby operating the pacemaker at reduced battery energy drain, periodically monitoring said threshold characteristic in a patient and dynamically producing said modified pacing pulses to follow changes in the monitored threshold characteristic, and following the changes by varying the width of the pacing pulses in a range above chronaxie.

4. The method of controlling a battery operated cardiac pacemaker implant to produce low energy pacing stimulus pulses at an implanted heart stimulus electrode to conserve battery power, comprising in combination the steps of:

performing threshold measurements at at least two different stimulus pulse energy levels at the implanted electrode of a particular patient and organizing said stimulus pulses into effective and ineffective energy levels for producing heartbeats, determining from the threshold measurements an individual energy threshold characteristic for the particular pacemaker system and patient under test by calculating from said different energy level measurements a substantially most energy efficient stimulus pulse in the implanted pacemaker effective to stimulate the heart, determining the threshold characteristic by establishing a minimum energy pulse width that produces a heartbeat with stimulus pulses of two different amplitudes defining a hyperbolic curve representative of the threshold characteristic, adjusting the energy efficient stimulus pulse to the technical capability of the particular pacemaker for operating that pacemaker with a modified optimum energy stimulus pulse exceeding the minimum energy threshold by a predetermined safety margin, and producing in the pacemaker said modified stimulus pulse, thereby operating the pacemaker at reduced battery energy drain.

5. The method of claim 1 further comprising the step of determining at least part of the steps by monitoring means external to said pacemaker implant, thereby to reduce battery drain of the implanted pacemaker.

6. The method of claim 1 wherein all the steps are determined automatically and periodically by means of internal means in the implanted pacemaker.

7. The method of extending the battery life of a battery operated implanted pacemaker producing stimulation pulses at an implanted electrode comprising the steps of determining characteristic pulses with a substantially most energy efficient width and amplitude characteristic for stimulating the heart in a particular patient with a particular pacemaker and implanted pacing electrode, and adjusting the implanted pacemaker to produce stimulation pulses with a width and amplitude at an energy level exceeding the most efficient energy characteristic by a predetermined safety margin.

8. The method of extending the battery life of a battery operated implanted pacemaker producing stimulation pulses at an implanted electrode comprising the steps of determining a threshold characteristic of pulses with a minimum energy for stimulating the heart in a particular patient with a particular pacemaker and implanted pacing electrode, adjusting the implanted pacemaker to produce stimulation pulses with a width and amplitude at an energy level exceeding the minimum energy threshold characteristic by a predetermined safety margin, and determining the threshold characteristic periodically and dynamically for automatic adjustment of the energy of the stimulation pulses in response to changes in the threshold characteristic.

9. The method of extending the battery life of a battery operated implanted pacemaker producing stimulation pulses at an implanted electrode comprising the steps of determining a threshold characteristic of pulses with a minimum energy for stimulating the heart in a particular patient with a particular pacemaker and implanted pacing electrode,  adjusting the implanted pacemaker to produce stimulation pulses with a width and amplitude at an energy level exceeding the minimum energy threshold characteristic by a predetermined safety margin,  determining the threshold characteristic periodically and dynamically for automatic adjustment of the energy of the stimulation pulses in response to changes in the threshold characteristic, and  changing the energy of the stimulation pulses by varying the pulse widths in a range exceeding chronaxie.

10. A battery operated cardiac pacemaker system for producing pacing pulses at an implanted stimulation electrode at an energy level attaining extended pacemaker battery life, comprising in combination,  monitoring means for determining a stimulation threshold characteristic by analyzing effective and ineffective stimulation pulses for a particular implanted pacemaker and implanted stimulation electrode,  logic means for determining the operating conditions of the particular implanted pacemaker for producing stimulation pulses of variable energy content,  calculating means for establishing a substantially most energy efficient stimulation pulse characteristic for the particular implanted pacemaker and electrode at a pulse energy level exceeding the minimum effective pulse energy level for stimulation by a predetermined safety level, and  pacing pulse energy control means for automatically responding to produce the established energy efficient stimulation pulses as pacemaker pacing pulses.

11. A battery operated cardiac pacemaker system for producing pacing pulses at an implanted stimulation electrode at an energy level attaining extended pacemaker battery life, comprising in combination,  monitoring means for determining a stimulation threshold characteristic by analyzing effective and ineffective stimulation pulses for a particular implanted pacemaker and implanted stimulation electrode,  logic means for determining the operating conditions of the particular implanted pacemaker for producing stimulation pulses of variable energy content,  calculating means for establishing an optimum stimulation pulse energy for the particular implanted pacemaker and electrode at a pulse energy level exceeding the minimum effective pulse energy level by a predetermined safety level,  pacing pulse energy control means for automatically responding to the optimum stimulation pulse energy for producing pacemaker pacing pulses, and  means for adjusting the pacing pulse energy by varying the width of the pulses in a range exceeding chronaxie.

12. A battery operated cardiac pacemaker system for producing pacing pulses at an implanted stimulation electrode at an energy level attaining extended pacemaker battery life, comprising in combination,  monitoring means for determining a stimulation threshold characteristic by analyzing effective and ineffective stimulation pulses for a particular implanted pacemaker and implanted stimulation electrode,  logic means for determining the operating conditions of the particular implanted pacemaker for producing stimulation pulses of variable energy content,  calculating means for establishing an optimum stimulation pulse energy for the particular implanted pacemaker and electrode at a pulse energy level exceeding the minimum effective pulse energy level by a predetermined safety level,  pacing pulse energy control means for automatically responding to the optimum stimulation pulse energy for producing pacemaker pacing pulses, and  means responsive to two pulses of varying width to determine points on a threshold characteristic curve identifying an algorithm for controlling the pacing pulse energy.

13. The pacemaker system of claim 10 further comprising periodically actuated means for monitoring the threshold characteristic and dynamically adjusting the pulse energy in response to the monitored threshold characteristic.

14. The pacemaker system of claim 10 further comprising said monitoring means external to an implanted pulse producing pacemaker including telemetering means for adjusting the pacing pulses to conform with the monitored threshold characteristic.

15. An improved low energy implanted battery operated pacemaker system comprising in combination means for monitoring in-situ a particular implanted pacemaker and stimulus electrode to determine a substantially most energy efficient stimulus pulse characteristic effective to stimulate the heart and means for adjusting the pacemaker responsive to said energy efficient stimulus pulse to produce pacing pulses of such characteristic at an energy level exceeding the threshold by a predetermined safety margin to thereby establish an improved battery life.

16. A control system for an energy efficient battery operated pacemaker implanted in a particular patient, comprising in combination,  programming means external to said implanted pacemaker,  bidirectional communication means between the programming means and the pacemaker,  analyzing means to discriminate between pacing pulses ineffective and effective to stimulate the heart,  logic means to determine automatically in response to the analyzing means an optimum energy efficient setting of pacing pulse width and amplitude for the implanted pacemaker-electrode system in said particular patient, and  adjusting means operable by said programming means to adjust in the implanted pacemaker the pacing pulse width and amplitude to said optimum setting to achieve long life battery operation.

17. The system of claim 16 wherein the optimum setting consists of a minimum energy setting adapted to the technical capacity of the implanted pacemaker increased by a predetermined safety margin.

18. The system of claim 16 wherein the external programming means comprises display indicating means for providing pacemaker implant derived data communicated over said communicating means for visual display of such data to a supervising operator.

* * * * *